United States Patent
Sherry

(10) Patent No.: US 8,444,688 B2
(45) Date of Patent: May 21, 2013

(54) COVERED STENTS WITH DEGRADABLE BARBS

(75) Inventor: John Sherry, Needham, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 479 days.

(21) Appl. No.: 12/140,177

(22) Filed: Jun. 16, 2008

(65) Prior Publication Data

US 2008/0249598 A1    Oct. 9, 2008

Related U.S. Application Data

(63) Continuation of application No. 10/219,979, filed on Aug. 16, 2002, now abandoned.

(51) Int. Cl.
*A61F 2/82* (2006.01)
(52) U.S. Cl.
USPC ............................. 623/1.36; 623/1.38
(58) Field of Classification Search
USPC ............. 623/1.11–1.13, 1.15, 1.36, 1.2, 1.22, 623/1.34, 1.35, 1.38, 1.51–1.53; 606/200, 606/108, 198
See application file for complete search history.

(56) References Cited

U.S. PATENT DOCUMENTS

| | | | |
|---|---|---|---|
| 3,833,002 A | 9/1974 | Palma | |
| 4,655,771 A | 4/1987 | Wallsten | |
| 4,954,126 A | 9/1990 | Wallsten | |
| 5,026,377 A | 6/1991 | Burton et al. | |
| 5,061,275 A | 10/1991 | Wallsten et al. | |
| 5,167,614 A * | 12/1992 | Tessmann et al. | 623/1.15 |
| 5,201,757 A | 4/1993 | Heyn et al. | |
| 5,540,712 A * | 7/1996 | Kleshinski et al. | 623/1.19 |
| 5,630,840 A | 5/1997 | Mayer | |
| 5,645,559 A | 7/1997 | Hachtman et al. | |
| 5,888,201 A | 3/1999 | Stinson et al. | |
| 5,902,317 A | 5/1999 | Kleshinski et al. | |
| 5,980,564 A | 11/1999 | Stinson | |
| 6,042,578 A | 3/2000 | Dinh et al. | |
| 6,156,064 A * | 12/2000 | Chouinard | 623/1.44 |
| 6,174,330 B1 | 1/2001 | Stinson | |

(Continued)

FOREIGN PATENT DOCUMENTS

| JP | 10-510200 | 10/1998 |
|---|---|---|
| JP | 10-510200 A | 10/1998 |

(Continued)

OTHER PUBLICATIONS

Japanese Official Action for Patent Application No. 2004-529264, with English translation of Decision of Rejection.

*Primary Examiner* — Elizabeth Houston
(74) *Attorney, Agent, or Firm* — Vidas, Arrett & Steinkraus, P.A.

(57) ABSTRACT

The present invention is directed at a removable stent for providing reinforcement to a selected region of a selected body lumen including a resilient cylindrical layer, including at least one bioresorbable extrusion exterior from the resilient cylindrical layer for resisting migration of the removable stent when the removable stent is positioned in the selected region of the selected body lumen. The present invention also includes a temporary implantable endoprosthesis which includes a tubular, radially compressible and axially flexible structure, including at least one bioresorbable extrusion exterior from the resilient cylindrical layer for resisting migration of the removable stent when the removable stent is positioned in the selected region of the selected body lumen.

12 Claims, 5 Drawing Sheets

U.S. PATENT DOCUMENTS

| | | |
|---|---|---|
| 6,228,111 B1 | 5/2001 | Tormala et al. |
| 6,245,103 B1 | 6/2001 | Stinson |
| 6,254,609 B1 | 7/2001 | Vrba et al. |
| 6,383,214 B1 | 5/2002 | Banas et al. |
| 6,645,226 B1 * | 11/2003 | Jacobs et al. .................. 606/215 |
| 2001/0039450 A1 | 11/2001 | Pavcnik et al. |
| 2002/0103527 A1 | 8/2002 | Kocur et al. |
| 2004/0034407 A1 | 2/2004 | Sherry |

FOREIGN PATENT DOCUMENTS

| | | |
|---|---|---|
| WO | 96/38101 A1 | 12/1996 |
| WO | 9638101 | 12/1996 |
| WO | 9716133 | 5/1997 |

\* cited by examiner

COVERED STENTS WITH DEGRADABLE BARBS

CROSS REFERENCE TO RELATED APPLICATIONS

This application is a continuation and claims priority of U.S. patent application Ser. No. 10/219,979 filed Aug. 16, 2002 and is related to an application entitled "Disintegrating Stent and Method of Making Same," Ser. No. 09/592,413, by Jonathan Stinson, filed Jun. 13, 2000, the entire contents of both applications being hereby incorporated by reference.

BACKGROUND

1. Field of the Invention

The present invention relates generally to implantable medical prostheses which incorporate an anchoring mechanism to reduce or eliminate migration of the prostheses.

2. Description of Related Art

Medical prostheses frequently referred to as stents are well known and commercially available. These devices are used within body vessels of humans for a variety of medical applications. Examples include intravascular stents for treating stenoses, stents for maintaining openings in the urinary biliary, tracheobronchial, esophageal, and renal tracts, and vena cava filters. Stents may also be used by physicians for malignant tumors. Benign tumors are seldom stented with metal platforms.

Typically, a stent is delivered into position at a treatment site in a compressed state using a delivery device. After the stent is positioned at the treatment site, the delivery device is actuated to release the stent. Following release of the stent, self-expanding stents are allowed to self-expand within the body vessel. Alternatively, a balloon may be used to expand other types of stents. This expansion of the stent in the body vessel helps to retain the stent in place and prevent movement or migration of the stent. Stents are typically composed of stent filaments.

Stents may be categorized as permanent, removable or bioresorbable. Permanent stents are retained in place and incorporated into the vessel wall. Removable stents are removed from the body vessel when the stent is no longer needed. A bioresorbable stent may be composed of, or include, biogradable material or bioresorbable material which is broken down by the body and absorbed or passed from the body when it is no longer needed.

Commonly used materials for known stent filaments include Elgiloy(R) and Phynox(R) metal spring alloys. Other metallic materials that may be used for stents filaments are 316 stainless steel, MP35N alloy and superelastic Nitinol nickel-titanium Another stent, available from Schneider (USA) Inc. of Minneapolis, Minn., has a radiopaque clad composite structure such as shown in U.S. Pat. No. 5,630,840 to Mayer. Stents can also be made of a titanium alloy as described in U.S. Pat. No. 5,888,201.

Bioabsorbable implantable endoprostheses such as stents, stent-grafts, grafts, filters, occlusive devices, and valves may be made of poly(alpha-hydroxy acid) such as poly-L-lactide (PLLA), poly-D-lactide (PDLA), polyglycolide (PGA), polydioxanone, polycaprolactone, polygluconate, polylactic acid-polyethylene oxide copolymers, modified cellulose, collagen, poly(hydroxybutyrate), polyanhydride, polyphosphoester, poly(aminoacides), or related copolymers materials, each of which have a characteristic degradation rate in the body. For example, PGA and polydioxanone are relatively fast-bioabsorbing materials (weeks to months) and PLA and polycaprolactone are a relatively slow-bioabsorbing material (months to years).

Stents may also be covered with various materials to encourage or inhibit tissue attachment to the stent. Covered stents are gaining, favor for biliary applications because they more effectively inhibit tissue attachment, intrusion, and constriction of the tract than bare stents. For example, polytetrafluoroethylene (PTFE) covered stents are desirable for removable stents because tissue attachment or in-growth is reduced in comparison to bare stent or a stent covered with textile (polyester) material. Laminated ePTFE may also be used to cover stents.

As stents are covered with material to aid in their removal, stent migration from the treatment site increases. There remains a continuing need for covered stents which include characteristics to maintain the stent in position at the treatment site. For example, stents covered with ePTFE, such as Precedent, are easily removed after a given time period, such as six months, but may not provide sufficient fixation to prevent the risk of migration during the six month period.

SUMMARY

The present invention relates to a removable stent for providing reinforcement to a selected region of a selected body lumen including a resilient cylindrical layer. The improvement to the stent is the inclusion of at least one bioresorbably extrusion exterior from the resilient cylindrical layer for resisting migration of the stent when the stent is positioned in the selected region of the selected body lumen.

Another embodiment of the present invention includes at least one bioresorbable extrusion exterior from a resilient cylindrical layer of a temporary implantable endoprosthesis. The bioresorbable extrusion exterior to the resilient cylindrical layer resists migration of the stent when the stent is positioned in a selected region of a selected body lumen.

The present invention also includes a method of reducing migration of a removable stent which includes the steps of constructing a removable stent including a resilient cylindrical layer and placing at least one bioresorbable extrusion exterior from the resilient cylindrical layer on the stent. The removable stent is then positioned and expanded within a body lumen. Migration of the stent is resisted by the interaction between the at least one biosorbable extrusion and the body lumen.

BRIEF DESCRIPTION OF THE DRAWINGS

We first briefly describe the drawings.

FIG. 4 is an isometric view of an example of a metal spring alloy stent comprised of a single helical coil that a bioresorbable extrusion of the present invention may be used in connection with;

DETAILED DESCRIPTION

The present invention improves the fixation characteristics of removable stents by incorporating bioresorbable or bioabsorbable barbs onto the removable stent or a covered stent to anchor the stent during the service life of the stent.

Figure 1:
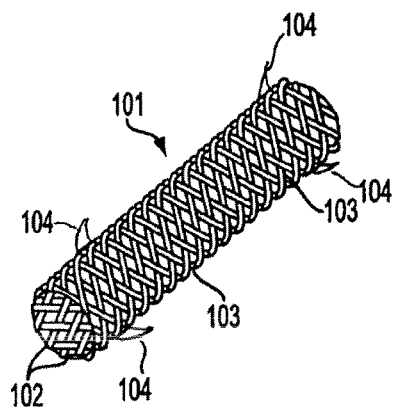
FIG. 1 is an isometric view of an example of a braided nitinol stent, comprised of 0.25 mm single filament strands that incorporates bioresorbable extrusions of the present invention.
Figure 2:
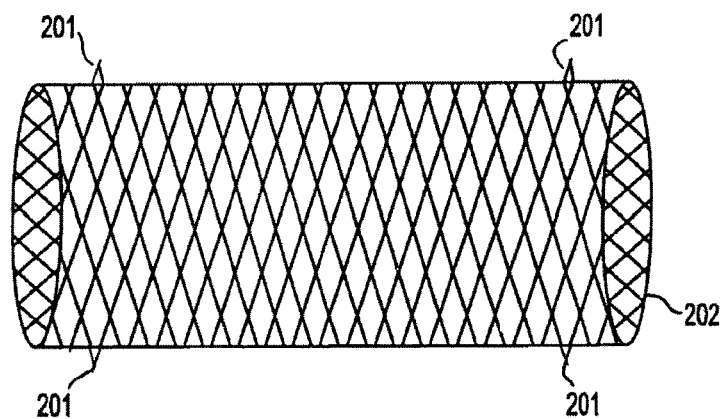
FIG. 2 is a simplified representation of a braided tubular stent of the type illustrated in FIG. 1 incorporating bioresorbable extrusions of the present invention.
Figure 3:
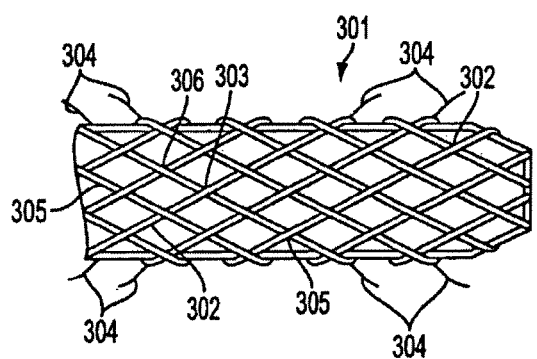
FIG. 3 illustrates another stent incorporating another bioresorbable extrusion of the present invention.
Figure 4:
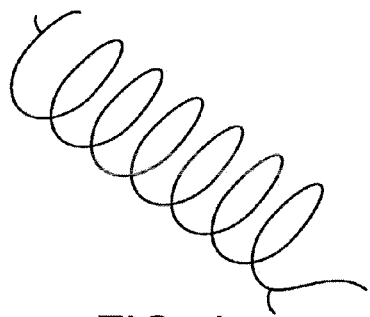
Figure 5:
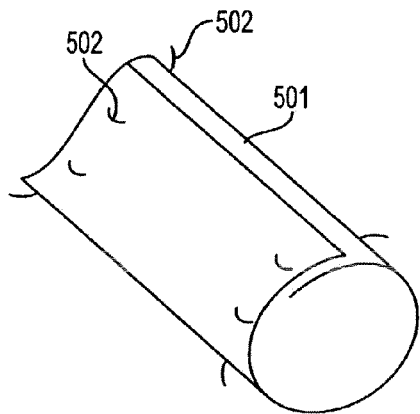
FIG. 5 is an isometric view of a rolled film or sheet-type bioabsorbable stent that may be used in connection with the bioresorbable extrusion of the present invention.
Figure 6:
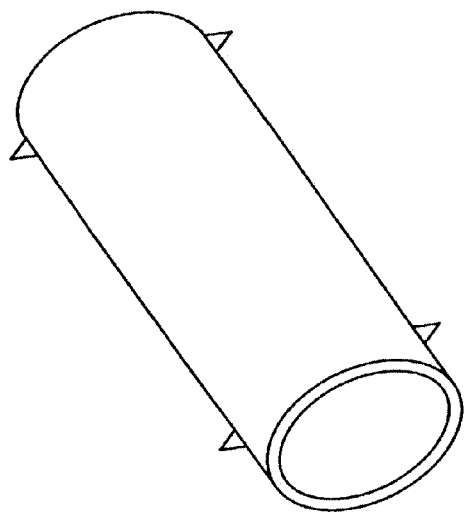
FIG. 6 is an isometric view of a solid extruded or molded tube-type stent that may be used in connection with the bioresorbable extrusion of the present invention.
Figure 7:
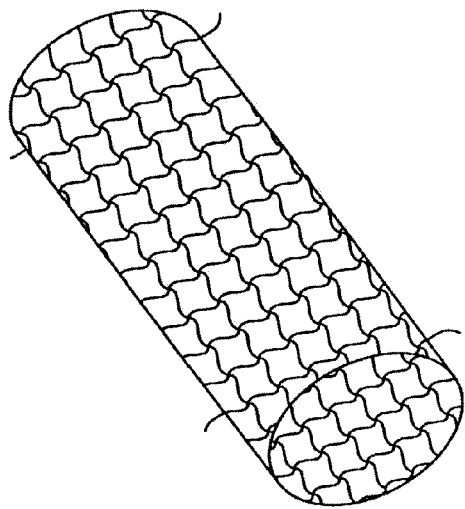
FIG. 7 is an isometric view of a knitted or woven polymer filament-type stent that may be used in connection with bioresorbable extrusion of the present invention.

An implantable prosthesis or stent 101 according to a preferred embodiment of the present invention is illustrated generally in FIGS. 1 through 3. Each of these figures includes a removable stent body with bioresorbable exterior extrusions added which, when placed in a body lumen, resist migration of the stent. FIG. 4 shows an alternative embodiment of the invention according to which the removable stent is comprised of a single helical coil of a metal spring alloy and the bioresorbable exterior extrusion is in the shape of a barb, angled to prevent migration of the stent once placed in a body lumen. FIG. 5 shows an alternative embodiment of the invention according to which the removable stent is comprised of a rolled film or sheet and the bioresorbable exterior extrusions are positioned circumferentially around the exterior of the stent. FIG. 6 shows an alternative embodiment of the invention according to which the removable stent is comprised of a solid extruded or molded tube and the bioresorbable exterior extrusions are triangular in shape to resist migration of the stent in any direction. FIG. 7 shows an alternative embodiment of the invention according to which the removable stent is comprised of knitted or woven metal filaments and the bioresorbable exterior extrusions are in the shape of barbs curved towards the ends of the stent. Removable stent bodies of the type illustrated in FIGS. 4-7, (without the bioresorbable exterior extrusions) are generally well-known in the art and may be manufactured according to well-known methods. The bioresorbable exterior extrusions may be added to the removable stents after the body of the removable stent is constructed or may be manufactured as part of the removable stent body. Any of the removable stents according to the embodiments of FIGS. 1-7 may be made using biostable material such as Elgiloy(R) or Phynox(R) metal spring alloys, 316 stainless steel, MP35N alloy, superelastic Nitinol nickel-titanium or similar non-bioresorbable materials.

Referring again to the preferred embodiment of FIGS. 1 through 3, removable stent 101 is a tubular device formed from two sets of oppositely-directed, parallel, spaced-apart and helically wound elongated strands or filaments 102. The removable stent body of FIGS. 1 and 2 is described in more detail in U.S. patent application Ser. No. 08/904,967, filed Aug. 1, 1997. In particular, the sets of filaments 102 are interwoven in an over and under braided configuration intersecting at points such as 103 to form an open mesh or weave construction. Methods for fabricating the body of removable stents 101 are generally known and disclosed, for example, in the Wallsten U.S. Pat. No. 4,655,771 and the Wallsten, et al. U.S. Pat. No. 5,061,275.

Removable stent 101 is shown in its expanded or relaxed state in FIGS. 1 and 2, i.e., in the configuration it assumes when subject to no external loads or stresses. The filaments 102 are resilient, permitting the radial compression of removable stent 101 into a reduced-radius, extended-length configuration or state suitable for delivery to the desired placement or treatment site through a body vessel (i.e., transluminally). Removable stent 101 may also be self-expandable from the compressed state, and axially flexible. Bioresorbable exterior extrusions 104 are also resilient permitting bioresorbable exterior extrusions 104 to be contained within a delivery device when removable stent 101 is in a compressed state but expanded to the relaxed state as shown in FIGS. 1 and 2. Bioresorbable exterior extrusions 104 are also inflexible enough, so that when in the expanded state in a body lumen, bioresorbable exterior extrusions 104 prevent migration of removable stent 101 within body lumen. According to one embodiment of the invention, at least one and preferably all bioresorbable extrusions is composed of one or more commercially available grades of polylactide, poly-L-lactide (PLLA), poly-D-lactide (PDLA), polyglycolide (PGA), polydioxanone, polycaprolactone, polygluconate, polylactic acid-polyethylene oxide copolymers, modified cellulose, collagen, poly(hydroxybutyrate), polyanhydride, polyphosphoester, poly(amino acids), poly(alpha-hydroxy acid) or related copolymers materials.

According to one embodiment of the invention, removable stent 101 may be a radially and axially flexible tubular body having a predetermined diameter that is variable under axial movement of the ends of the body relative to each other. Removable stent 101 may be composed of a plurality of individually rigid but flexible and elastic thread elements or filaments 102, each of which may extend in a helix configuration along a longitudinal center line of the body as a common axis. The filaments 102 may define a radially self-expanding body. The body may be provided by a first number of filaments 102 having a common direction of winding but axially displaced relative to each other, and crossing a second number of filaments 102 also axially displaced relative to each other but having an opposite direction of winding. Bioresorbable exterior extrusions 104 are flexible in the axially direction of removable stent 101, but rigid in the longitudinal direction. The flexibility of bioresorbable exterior extrusions 104 in the axial direction allows removable stent 101, including bioresorbable exterior extrusions 104 to be compressed into a delivery device. The center line common axis or longitudinal direction of removable stent 101 and the axial (or axially) direction are different and not parallel. Axial (or axially) directions are situated around an axis, in this case the longitudinal direction. Therefore, by including both compression of bioresorbable exterior extrusions 104 in an axial (or axially) direction along with compression of removable stent 101 has each flexible bioresorbable exterior extrusion 104 wrapped in a non-longitudinal direction around the compressed removable stent 101. The rigidity of bioresorbable exterior extrusions 104 in the longitudinal direction of removable stent 101 ensures that, once removable stent 101 is positioned in a body lumen, bioresorbable exterior extrusions 104 will resist migration of removable stent 101 within the body lumen.

Bioresorbable exterior extrusions 104 may take a variety of shapes. Bioresorbable exterior extrusions 104 of FIG. 1 are in the shape of a barb with the concave surface of the barb towards the center of removable stent 101. Alternatively, bioresorbable exterior extrusions 201 of FIG. 2 may be triangular in shape and rigid in the longitudinal direction of removable stent 202 to resist migration in a longitudinal direction once removable stent 202 is positioned within a body lumen.

Removable stent 301 of FIG. 3 includes a plurality of individually rigid but flexible and elastic thread elements or filaments 302, each of which may extend in a helix configuration along a longitudinal center line of the body as a common axis. The filaments 302 may define a radially self-expanding body. The body may be provided by a first number of filaments 302 having a common direction of winding but axially displaced relative to each other, and crossing a second number of filaments 305 also axially displaced relative to each other but having an opposite direction of winding. Bioresorbable exterior extrusions 304 are flexible in the axially direction of removable stent 301, but rigid in the longitudinal direction. The flexibility of bioresorbable exterior extrusions 304 in the axial direction allows removable stent 301, including bioresorbable exterior extrusions 304 to be compressed into a delivery device. Filaments 302 and filaments 305 may be configured to alternate at intersections. For example, at one intersection filament 302 may be exterior to filament 305 as shown at 303. Alternatively, filament 305 may be exterior to filament 302 at other intersections as shown at 306. FIG. 3 also shows that a number of bioresorbable exterior extrusions may be included in an embodiment to further resist migration of removable stent 301 when placed within a body lumen.

FIGS. 3 through 7 show other embodiments of the placement of bioresorbable exterior extrusions on various removable stent configurations. Notably, FIG. 5 depicts bioresorbable exterior extrusions 502 along an outer circumference of removable stent 501. Note that many orientations and configurations of bioresorbable exterior extrusions may be configured to resist migration of the stent within a body lumen.

Note also that bioresorbable exterior extrusions of the present invention may be used to resist migration of other types of removable stents. Other stent structures and features may be include, for example, stents having features which enhance or cooperate with the tubular and self-expandable structure or which facilitate the implantation of the structure. One example is the inclusion of radiopaque markers on the structure which are used to visualize the position of the stent through fluoroscopy during implantation. Other examples include collapsing threads or other structures to facilitate repositioning of the stent.

Note that the use of bioresorbable exterior extrusions on a removable stent would help ensure the proper position of the removable stent during its in service, or in the lumen, time. By selection of the proper bioresorbable materials, when the time to remove the removable stent has arrived, the bioresorbable exterior extrusions have been absorbed into, or broken down by the body, allowing for easy removal.

Note also that a non-bioresorbable exterior extrusion attached to the removable stent body with bioabsorbable material may also be used in the implementation of the present invention.

Figure 8:
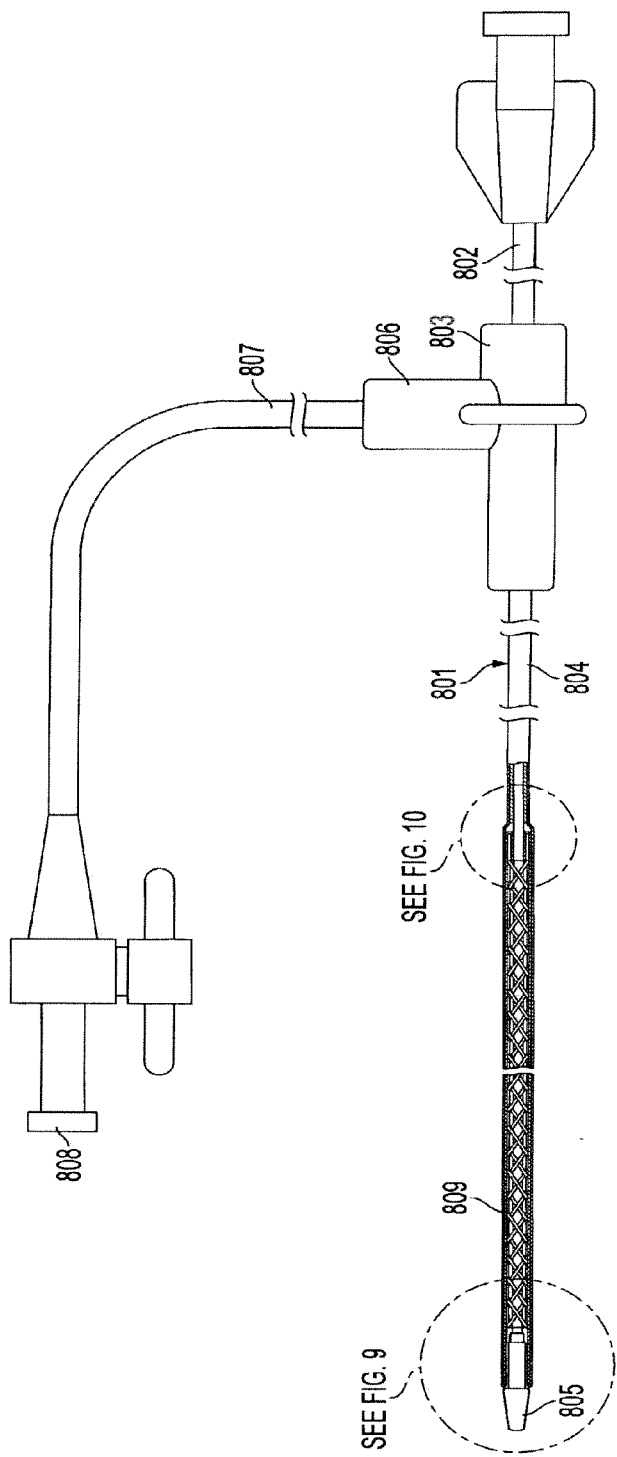
FIG. 8 is a side view of a delivery device with the sent shown in FIG. 1 loaded thereon.
Figure 10:
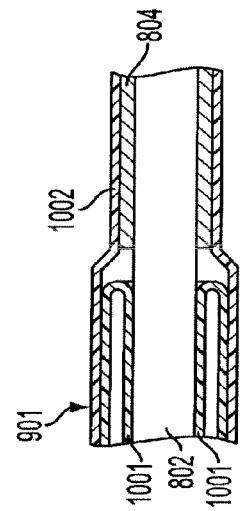
FIG. 10 is a detailed view of the portion of the delivery device encircled at "FIG. 10" in FIG. 8.
Figure 9:
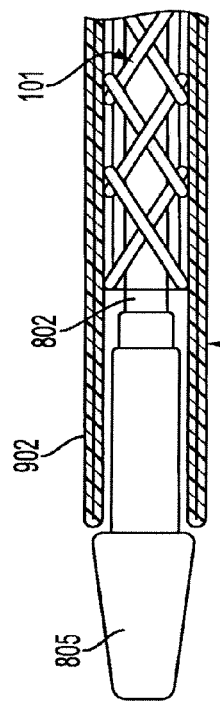
FIG. 9 is a detailed view of the portion of the delivery device encircled at "FIG. 9" in FIG. 8.
Figure 11:
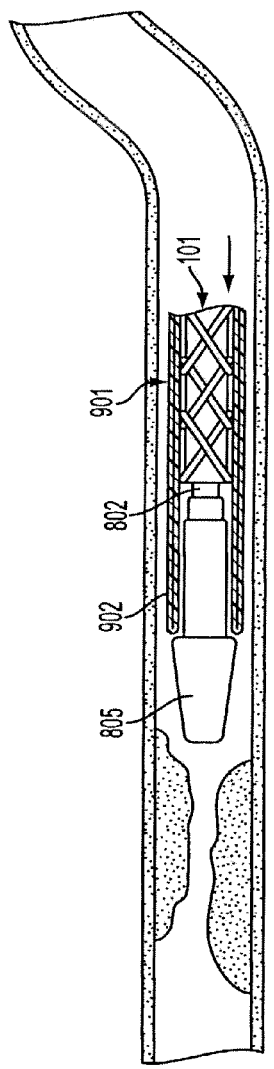
FIGS. 11-14 are partial cross-sectional side views of the distal portion of the delivery device and stent shown in FIG. 8 at various stages during a stent deployment operation in a body vessel.
Figure 12:
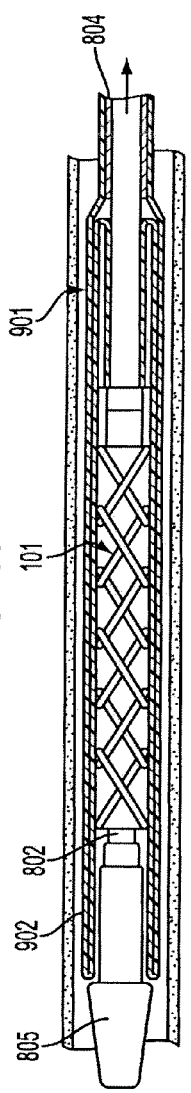
Figure 13:
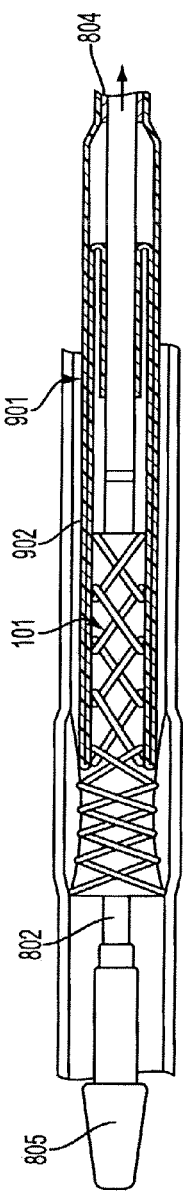
Figure 14:
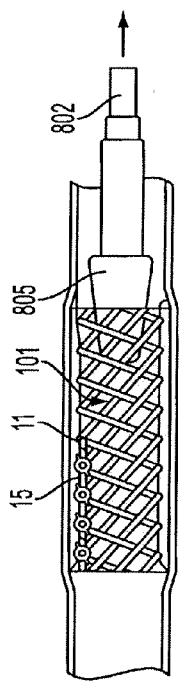

FIGS. 8 through 10 are illustrations of a delivery device 801 for delivering removable stent 101 to a treatment site in a body vessel. As shown, removable stent 101 is carried by the distal portion 809 of delivery device 801, and is placed on the delivery device in a radially contracted or compressed state. The proximal portion of delivery device 801 generally remains outside of the body for manipulation by the operator.

Delivery device 801 includes an elongated, inner tube 802, preferably having an axially extending lumen therethrough. The distal portion 809 of inner tube 801 is flexible and can be made from nylon or other suitably flexible biocompatible polymeric material. At its distal end, inner tube 801 is provided with a head 805. Head 805 serves to facilitate the insertion of delivery device 801 through a narrow opening in a body vessel. The proximal portion of inner tube 802 is preferably formed from stainless steel or other suitably rigid metal alloy. The proximal end of the distal portion of inner tube 802 is bonded to the distal end of the proximal portion of the inner tube in any conventional manner such as by using a standard adhesive.

A proximal tube 804 surrounds the proximal portion of inner tube 802 in coaxial fashion. Proximal tube 804 is preferably formed from polyurethane. The proximal end of tube 804 is connected to a valve body 803 having a side port 806. An extension tube 807 extends from side port 806 to an opening 808. This arrangement allows fluid to be injected through extension tube 807 and between proximal tube 804 and inner tube 802.

A moveable hose 901 surrounds the distal portion of inner tube 802. Hose 901 is rolled over itself to form a double-walled section. The proximal end of inner wall 1001 of a double-walled section is connected directly to inner tube 802. The proximal end of the outer wall 1002 of the double-walled section is connected to the outer surface of the distal portion of proximal tube 804. These connections can be achieved by any conventional means such as by a standard adhesive. This arrangement allows hose 901 to be rolled off removable stent 101 and placed on the distal portion of inner tube 802. By moving valve body 803 in the proximal direction, outer wall 1002 of hose 901 slides proximally over inner wall 1001. This causes inner wall 1001 to "roll back" off of removable stent 101. To facilitate movement of hose 901 off of removable stent 101, at least that portion of inner wall 1001 that contacts outer wall 1002 in the area where hose 901 is rolled over to form the double-walled section should be lubricious. The lubricious characteristic can be achieved by adding a lubricious substance to this surface of hose 901, injecting a lubricious liquid between inner wall 1001 and outer wall 1002 or forming hose 901 from a naturally slippery material such as Teflon coating.

At least the surfaces of inner wall 1001 and outer wall 1002 that face each other in the double-walled section are coated with a lubricious hydrophilic coating. In one embodiment the hydrophilic coating is 2018-M material available from Hydromer Inc. of Whitehouse, N.J. Other materials that can be used are polyethylene oxide and hyaluronic acid. When wet, the hydrophilic coating becomes lubricious and thus reduces friction between inner wall 1001 and outer wall 1002 of the double-walled section of hose 901 as outer wall 1002 moves past inner wall 1001. This facilitates the removal of the double-walled section of hose 901 from removable stent 101. Hydrophilic material may be added to hose 901 during the assembly of delivery device 801. To enable the hydrophilic material to adequately bond to hose 901, the material used to manufacture hose 901 should be matched to the hydrophilic material used. It has been found that polyurethane works well as a material for hose 901. In particular, a blend of 65D and 75D polyurethane provides sufficient flexibility to allow hose 901 to roll over itself yet still be soft enough and compatible with the hydrophilic material that it can be properly coated. In one embodiment, the blend is formed of 50% 65D polyurethane and 50% 75D polyurethane. During the assembly of delivery device 801, one side of hose 901 is coated with the hydrophilic material after the outer wall 1002 of the hose has been connected to proximal tube 804. Isopropyl alcohol is first applied to one side of hose 901 to clean the surface and remove the waxy film resulting from the plasticizers in the polyurethane. The same side of hose 901 is then coated with the hydrophilic material. The surface of hose 901 should be flushed with alcohol for about thirty seconds. Similarly, the surface of hose 901 should be flushed with the hydrophilic coating for about thirty seconds. It has been found that this technique deposits sufficient hydrophilic material on inner wall 1001 and outer wall 1002 to allow hose 901 to be rolled back with minimal friction when the hydrophilic material is wet.

After delivery device 801 has been assembled and is ready for use, the hydrophilic coating is wetted with physiological saline solution by injecting the solution through extension tube 807, past proximal tube 804 and into the space between inner wall 1001 and outer wall 1002 of the double-walled section of hose 901. Excess fluid exits from the hole 902 formed toward the distal end of the double-walled section of hose 901. In this same manner, a lubricious fluid such as polyethylene glycol can be injected into the space between inner wall 1001 and outer wall 1002 of the double-walled section to provide the lubricious characteristic of hose 901 in place of adding a lubricious hydrophilic material through hose 901 as described above.

The manner by which delivery device 801 is operated to deliver removable stent 101 to a treatment site in a body vessel or lumen including curved sections is illustrated in FIGS. 11-14. As shown, removable stent 101 is placed in a radially compressed state in a surrounding relationship to the outer distal end of inner tube 802. Removable stent 101 is constrained on inner tube 802 by the double-walled section of hose 901. It is important that removable stent 101 not be confined too tightly on inner tube 802. Hose 901 should apply just enough force to removable stent 101 to hold removable stent 101 in place. The double-walled section of hose 901 can be removed from around removable stent 101 by pulling valve body 803 and proximal tube 804 in a proximal direction. The double-walled section "rolls" off removable stent 101. No sliding movements take place between removable stent 101 and inner wall 1001 which contacts removable stent 101. Along with the movement of the double-walled section in a proximal direction, the distal end of removable stent 101 will be exposed in a radial direction to engagement against the wall of the body vessel. As the double-walled section of hose 901 continues moving proximally, more of removable stent 101 expands in a radial direction until the entire length of removable stent 101 is exposed and engages the wall of a body.

A lumen is used to enable delivery device 801 to follow a guide wire (not shown) previously inserted percutaneously into the body vessel. The lumen of inner tube 802 can also be used to introduce a contrast fluid to the area around the distal end of delivery device 801 so the position of delivery device 801 can be detected (e.g., through the use fluoroscopy or X-ray techniques).

Figure 15:
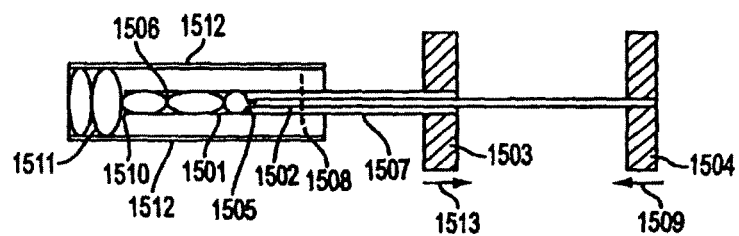
FIG. 15 is a side view of a pusher-type delivery device.

In FIG. 15 there is shown another embodiment of a delivery device which may be used to position stents including the present invention within a body lumen.

This assembly constitutes a flexible instrument intended to introduce the tubular body in contracted state into for example a blood vessel and then to expand the body when located therein. The parts of the instrument consist of an outer flexible tube 1501 and a concentric also flexible inner tube 1502. At one end of the outer tube an operational member 1503 is arranged. Another operational member 1504 is attached to the free end of inner tube 1502. In this manner the inner tube 1502 is axially displaceable in relation to the outer tube 1501. At the other end of inner tube 1502 a piston 1505 is attached which when moving runs along the inner wall of outer tube 1501.

When the instrument is to be used the tubular expansible body 1506 in contracted state is first placed inside tube 1501, the inner tube 1502 with the piston 1505 being located in the rear part 1507 of outer tube 1501. The starting position of piston 1505 is shown by dashed lines at 1508 in FIG. 15. In this manner part of tube 1501 is filled with the contracted tubular body 1506 in the starting position.

During implantation the flexible tubular part of the device is inserted to the location of a blood vessel intended for implantation. Member 1504 is then moved in the direction of arrow 1509, the contracted body 1506 being pushed out through end 1510 of tube 1501, the part of the tubular body 1506 leaving tube end 1510 expanding until in its expanded position 1511 it is brought to engagement with the interior of vascular wall 1512. The tubular body 1506, 1511 is for sake of simplicity shown in FIG. 15 as two sinus-shaped lines. To the extent that the expanded body 1506 comes into engagement with vascular wall 1512 tube end 1510 is moved by moving member 1503 in the direction of arrow 1513. The contracted body 1506 is moved by the piston 1505 pushing against one end of the body. Thus, the implantation takes place by simultaneous oppositely directed movements of members 1504 and 1503, the displacement of member 1504 being larger than that of member 1503. When the contracted body 1506 has been fully removed from the tube 1501 the expansion is terminated and the instrument can be removed from the location of the operation.

The delivery system according to FIG. 15 has the great advantage that the constructional details are quite simple and can be operated with high reliability. The instrument shown is also suitable for implantation of helices with very small diameters. As an example there may be mentioned that experiments have been performed with a tubular expansible body consisting of crossing thread elements, the contracted diameter of the body being only 2 mms and the expanded diameter 6 mms. It is also fully conceivable to implant expanded bodies with even smaller diameter. The instrument according to FIG. 15 may also advantageously be used for implantation of bodies in the form of grafts of a very large diameter.

In implantation of long bodies it is conceivable that the resistance in displacing same in tube 1501 becomes too high. In this case it may be suitable to replace piston 1505 at the front end of tube 1502 with movable jaws or latches which operate in such a manner that when tube 1502 is brought forward in the direction of arrow 1509 the latches engage the inner side of body 1506, the body being brought forward. When tube 1502 is brought back in the direction of arrow 1513 the latches are released. In this manner body 1506 can be moved forwardly by a pump-like motion of tube 1502.

Many embodiments of the different members shown in FIG. 15 are, of course, conceivable. Thus, it is possible for example to simplify implantation for the surgeon by controlling the relative motion between members 1503 and 1504 in a mechanical manner.

The stents of the present invention may be delivered by alternative methods or using alternative devices. For instance, the device described in Heyn et al. U.S. Pat. No. 5,201,757 may be utilized.

Although the present invention has been described with reference to preferred embodiments, those skilled in the art will recognize that changes can be made in form and detail without departing from the spirit and scope of the invention.

It will be evident from considerations of the foregoing that the devices of the present invention may be constructed using a number of methods and materials, in a wide variety of sizes and styles for the greater efficiency and convenience of a user.

The above described embodiments of the invention are merely descriptive of its principles and are not to be considered limiting. Further modifications of the invention herein disclosed will occur to those skilled in the respective arts and all such modifications are deemed to be within the scope of the invention as defined by the following claims.

The invention claimed is:

1. A removable stent for providing reinforcement to a selected region of a selected body lumen, said removable stent including a resilient cylindrical layer, said removable stent comprises:
   said removable stent in a first state being compressed to a smaller diameter than that of the selected body lumen to move said resilient cylindrical layer to an interior surface of the selected body lumen, and said removable stent in a second state being radially self-expanded; and,
   at least one bioresorbable barb extending from the resilient cylindrical layer, said at least one barb contacting the interior surface of the selected body lumen when said removable stent is expanded, the contact of said at least one barb with the interior surface of the selected body lumen resisting migration of the removable stent when said removable stent is positioned in said selected region of said selected body lumen, said at least one barb being flexible in a non-longitudinal direction about said stent, and said at least one barb being flexible to be bent around and toward said resilient cylindrical layer about the non-longitudinal direction so as to have both said resilient cylindrical layer and said at least one barb disposed in compression to a smaller diameter than the selected body lumen, and said at least one barb being rigid along one longitudinal direction of said stent, wherein said resilient cylindrical layer includes a woven over and under braided configuration, and wherein a portion of said at least one barb that is not connected to the resilient cylindrical layer is curved towards a first end of said stent to resist migration in said selected body lumen of said removable stent toward the first end of said stent.

2. The removable stent of claim 1 wherein said removable stent is composed of a non-bioresorbable material.

3. The removable stent of claim 1 wherein said removable stent and said at least one barb extending from said resilient cylindrical layer are part of a unitary design.

4. The removable stent of claim 1 wherein said removable stent is a covered stent.

5. The removable stent of claim 1 wherein said removable stent is a covered removable stent and said cover is composed of an expanded polytetrafluoroethylene.

6. The removable stent of claim 1 wherein said at least one bioresorbable barb is composed of material selected from the group consisting of polylactide, poly-L-lactide (PLLA), poly-D-lactide (PDLA), polyglycolide (PGA), polydioxanone, polycaprolactone, polygluconate, polylactic acid-polyethylene oxide copolymers, modified cellulose, collagen, poly (hydroxybutyrate), polyanhydride, polyphosphoester, poly (amino acids), and poly (alpha-hydroxy acid).

7. A temporary implantable endoprosthesis including a tubular, radially compressible and axially flexible stent structure, said temporary implantable endoprosthesis comprises:
   at least one bioresorbable barb extending from a resilient cylindrical layer of said stent, and said stent and said at least one barb in a first state being compressed to a smaller diameter than a selected region of a selected body lumen to move said resilient cylindrical layer and said at least one barb to an interior surface of the selected body lumen, and said stent and said at least one barb in a second state being radially self-expanded to secure said resilient cylindrical layer to an interior surface of the selected body lumen and also to expand said at least one barb to contact the interior surface of the selected body lumen to resist migration of said stent when said stent is positioned in a selected region of a selected body lumen, said at least one barb being flexible in a non-longitudinal direction about said stent, and said at least one barb being flexible to be bent around and toward said resilient cylindrical layer about the non-longitudinal direction so as to have both said resilient cylindrical layer and said at least one barb disposed in compression to a smaller diameter than the selected body lumen and said at least one barb being rigid along one longitudinal direction of said stent when said stent is expanded, wherein a portion of said at least one barb that is not connected to the resilient cylindrical layer is curved towards a first end of said stent to resist migration in said selected body lumen of said removable stent toward the first end of said stent, wherein degradation of said at least one bioresorbable barb is based on the period of time said stent is expected to remain inside a patient and wherein staid stent is a woven stent having an over and under braided configuration.

8. The temporary implantable endoprosthesis of claim 7 wherein said temporary implantable endoprosthesis is made of non-bioresorbable material.

9. The temporary implantable endoprosthesis of claim 7 wherein said stent and said at least one barb extending from said resilient cylindrical layer are part of a unitary design.

10. The temporary implantable endoprosthesis of claim 7 wherein said stent is a covered stent.

11. The temporary implantable endoprosthesis of claim 7 wherein said stent is a covered removable stent and said cover is composed of an expanded polytetrafluoroethylene.

12. The temporary implantable endoprosthesis of claim 7 wherein said at least one barb is composed of material selected from the group consisting of polylactide, poly-L-lactide (PLLA), poly-D-lactide (PDLA), polyglycolide (PGA), polydioxanone, polycaprolactone, polygluconate, polylactic acid-polyethylene oxide copolymers, modified cellulose, collagen, poly (hydroxybutyrate), polyanhydride, polyphosphoester, poly (amino acids), and poly (alpha-hydroxy acid).

* * * * *